(12) United States Patent
Webster

(10) Patent No.: US 6,527,003 B1
(45) Date of Patent: Mar. 4, 2003

(54) MICRO VALVE ACTUATOR

(75) Inventor: James Russell Webster, Hsinchu (TW)

(73) Assignee: Industrial Technology Research, Hsinchu (TW)

( * ) Notice: Subject to any disclaimer, the term of this patent is extended or adjusted under 35 U.S.C. 154(b) by 0 days.

(21) Appl. No.: 09/717,016

(22) Filed: Nov. 22, 2000

(51) Int. Cl.$^7$ ............................................. F16K 31/02
(52) U.S. Cl. .................. 137/15.18; 251/11; 251/129.01; 251/368
(58) Field of Search ........................ 251/11, 331, 368; 137/907, 15.18

(56) References Cited

U.S. PATENT DOCUMENTS 4,714,048 A * 12/1987 Jefferies et al. .......... 119/14.08
6,129,331 A * 10/2000 Henning et al. ............... 251/11

OTHER PUBLICATIONS

Anderson et al., Microfluidic Biochemical Analysis System, 4 pages.
Guerin et al., Miniature One–Shot Valve, pp. 425–428.
Anderson et al., A Miniature Integrated Device for Automated Multistep Genetic Assays; Apr. 15, 2000, 6 pages, Nucleic Acids Research, 2000, vol. 28, No. 12.
Lagally et al., Microfabrication Technology For Chemical and Biomedical Microprocessors; 2000, Micro Total Analysis Systems 2000, pp. 217–220.

* cited by examiner

Primary Examiner—Kevin Lee
(74) Attorney, Agent, or Firm—Bacon & Thomas

(57) ABSTRACT

A simple micro valve actuator is disclosed. The micro valve actuator of this invention comprises a sealed vacuum chamber. The micro valve is actuated by providing a current to a thin film heater, which in turn weakens and, under the atmospheric pressure differential, breaks a diaphragm sealing said vacuum chamber whereby the vacuum inside the chamber is released. By applying the micro valve actuator of this invention to a microfluidic channel with a micro valve, the resulting pressure differential deforms the section of the microchannel at the micro valve area and adjacent to the vacuum chamber so to change the flow inside the microchannel. In the preferred embodiments of this invention, the chamber may be prepared in a silicon, glass, or plastic substrate and a diaphragm is vacuum bonded to seal the chamber. The diaphragm may comprise a metallic gas-impermeable film. A releasing member comprising a thin-film metallic heater is then microfabricated on the diaphragm. The assembly so prepared may be bonded to a glass or plastic substrate that contains a microchannel in which a micro valve is prepared. The invented micro valve actuator is suited for a microfluidic platform in changing the flow in a microchannel.

36 Claims, 2 Drawing Sheets

MICRO VALVE ACTUATOR

FIELD OF THE INVENTION

The present invention relates to a micro valve actuator, especially to a micro valve actuator comprising a vacuum chamber.

BACKGROUND OF THE INVENTION

Miniature pumps and valves have been a topic of great interest in the past 10 years. Many different pump and valve designs have been implemented by micromachining of silicon and glass substrates. Pumps and valves with pneumatic, thermal-pneumatic, piezoelectric, thermal-electric, shape memory alloy, and a variety of other actuation mechanisms have been realized with this technology. Although such pumps to date have shown excellent performance as discrete devices, often the process for fabricating these pumps and valves are so unique that the devices cannot be integrated into a complex microfluidic system. Recently, paraffin actuated valves, and hydrogel actuated valves are being developed on the way to a more complex microfluidic platform.

Miniature analytical analysis systems, however, are demanding pumps and valves that are relatively small in size and can be integrated together on a single substrate. Systems to perform sample processing for DNA analysis are one such example. Such systems can require anywhere from 10–100 such pumps and valves to perform a variety of pumping, mixing, metering, and chemical reactions that are required to extract DNA from a sample, amplify the DNA, and analyze the DNA. To date no such technology exists to perform this type of microfluidic sample processing.

Anderson, et al. demonstrated the concept by using external air sources, external solenoid valves and a combination of thin film valves and vents on a plastic analysis cartridge. The entire sample handling for DNA extraction, in vitro transcription and hybridization was performed in a prototype system. See: "Microfluidic Biochemical Analysis System", Proceedings of Transducers '97, the 9th International Conference on Solid-State Sensors and Actuators, Chicago, Jun. 16–19, 1997, 477–480 and "A Miniature Integrated Device for Automated Multistep Genetic Assays", Nucleic Acids Research, 2000 Vol 28 N 12, e60.

Recently, Mathies et al. employed the same technology to perform a polymerase chain reaction (PCR) followed by a capillary electrophoresis (CE) analysis on the same device ("Microfabrication Technology for Chemical and Biochemical Microprocessors", A. van den Berg (ed.), Micro Total Analysis Systems 2000, 217–220). For applications in which sample contamination is of concern, such as diagnostics, disposable devices are very appropriate. In this case the manufacturing cost of such a device must be extremely low.

i-STAT corporation currently markets a disposable device that analyzes blood gases as well as a variety of ions. The i-STAT cartridge uses external physical pressure to break on-chip fluid pouches and pump samples over ion-selective sensors (i-STAT Corporation Product Literature, June 1998). In a similar manner, Kodak has developed a PCR-based HIV test in a disposable, plastic blister pouch (Findlay, J. B. et al., Clinical Chemistry, 39, 1927–1933 (1993)). After the PCR reaction an external roller pushes the PCR product followed by binding, washing and labeling reagents into a detection area where the PCR amplified product can be detected. The complexity of such systems as these is limited in part by the means of pressure generation. The simplicity of these approaches however is quite elegant.

Disposable, one-shot microfabricated valves have been implemented by a few researchers for diagnostic applications. Guerin et al. developed a miniature one-shot (irreversible) valve that is actuated by melting an adhesive layer simultaneously with the application of applied pressure of the fluidic medium. See: "A Miniature One-Shot Valve", Proceedings of IEEE conference on Micro-Electro-Mechanical Systems, MEMS '98, 425–428. In this invention, if the applied pressure is high enough the melted adhesive layer gives way and the fluid passes through the valve.

Another one-shot type valve has been developed by Madou et al. in their U.S. Pat. No. 5,368,704, "Micro-electrochemical Valves and Method". Here the valve is actuated by the electrochemical corrosion of a metal diaphragm.

While complex microfluidic systems have been demonstrated using external air supplies and solenoid valves, a need exists for complex microfluidic systems in more portable instrument platforms. It is thus necessary to provide an actuator that provides actuation sources and that can be equipped directly on the device in which the actuator is used.

OBJECTIVES OF THE INVENTION

The objective of the present invention is to provide a one-time micro valve actuator.

Another objective of this invention is to provide a micro valve actuator that is easy to prepare under a relatively low cost.

Another objective of this invention is to provide a micro valve actuator with a vacuum chamber.

Another objective of this invention is to provide a micro valve module wherein the actuation sources are directly prepared on the device itself Another objective of this invention is to provide a novel method for the preparation of a micro valve module comprising a vacuum chamber to actuate the valving functions.

SUMMARY OF THE INVENTION

According to the present invention, a simple micro valve actuator is disclosed. The micro valve actuator of this invention comprises a sealed vacuum chamber. The micro valve is actuated by providing a current to a thin film heater, which in turn weakens and, under the atmospheric pressure differential, breaks a diaphragm sealing said vacuum chamber whereby the vacuum inside said chamber is released. By applying the micro valve actuator of this invention to a microfluidic channel the resulting pressure differential deforms a section of the microchannel adjacent to the vacuum chamber so to change the flow inside the microchannel. In the preferred embodiments of this invention, the chamber may be prepared in a silicon, glass, or plastic substrate and a diaphragm is vacuum bonded to seal the chamber. The diaphragm may comprise a metallic gas-impermeable film. A releasing member comprising a thin-film metallic heater is then microfabricated on the diaphragm. The assembly so prepared may be bonded to a glass or plastic substrate that contains a microchannel in which a micro valve is prepared. The invented micro valve actuator is suited for a microfluidic platform in changing the flow in a microchannel.

These and other objectives and advantages of the present invention may be clearly understood from the detailed description by referring to the following drawings.

DETAILED DESCRIPTION OF THE INVENTION

According to the present invention, a simple micro valve actuator is provided. The micro valve actuator of this invention comprises a sealed vacuum chamber that generates a deforming force to a microchannel adjacent to the vacuum chamber when the vacuum inside the chamber is released The deforming force of the vacuum chamber is actuated a release member to release said vacuum by providing a current to a thin film heater positioned on a diaphragm sealing said vacuum chamber. The provided current weakens and, under the atmospheric pressure differential, punctures the diaphragm whereby the vacuum inside said chamber is released.

The micro valve actuator of this invention may be applied to a microfluidic network, such that the resulting pressure differential generated by the released vacuum can be used to actuate a valve in the microfluidic network.

The following is a detailed description of the embodiments of the micro valve actuator of this invention by referring to a microfluidic channel with a micro valve.

Figure 1:
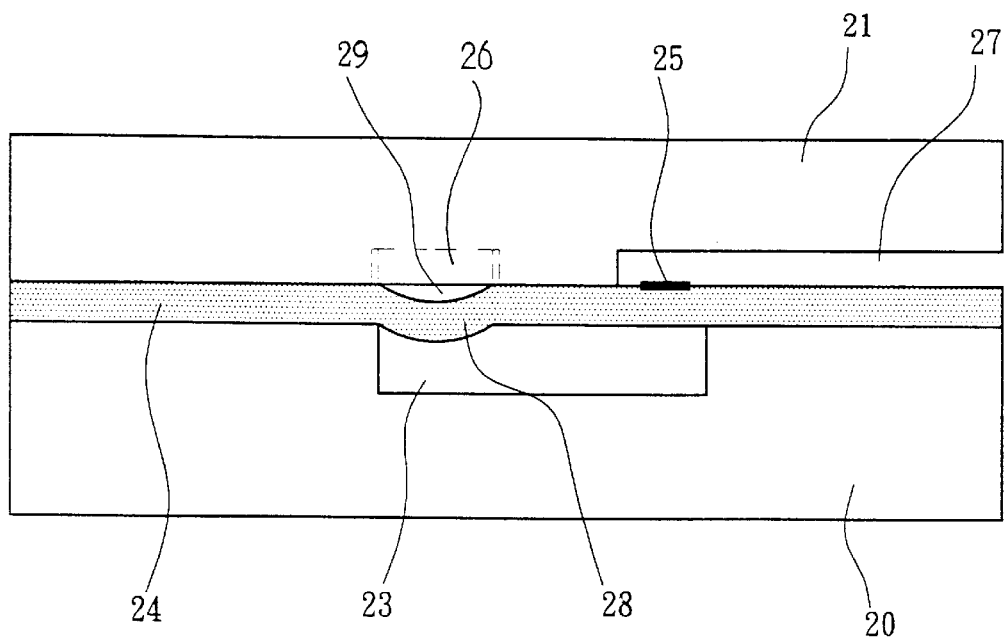
FIG. 1 shows the cross sectional view of a micro valve actuator of this invention prior to actuation.
Figure 2:
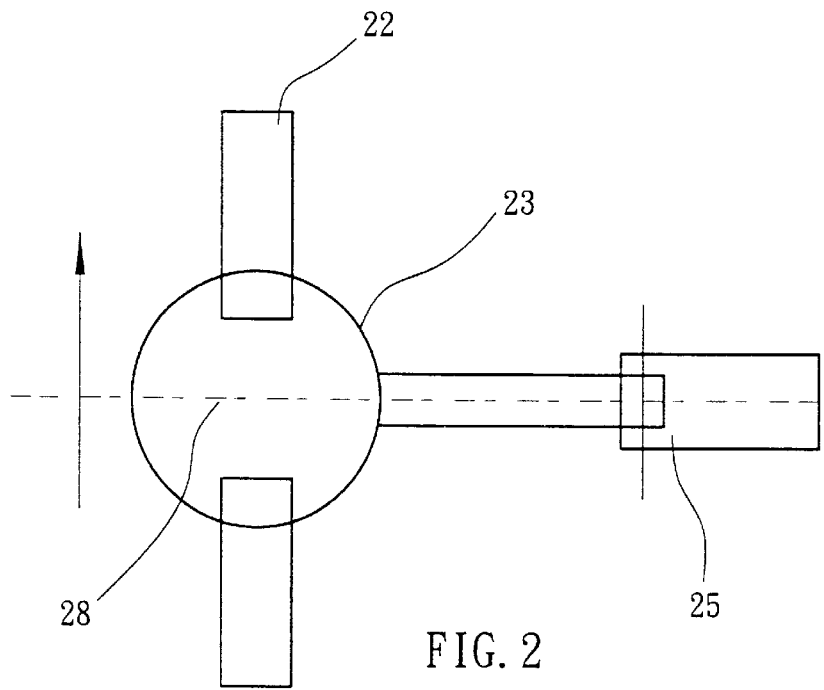
FIG. 2 shows its top view.
Figure 3:
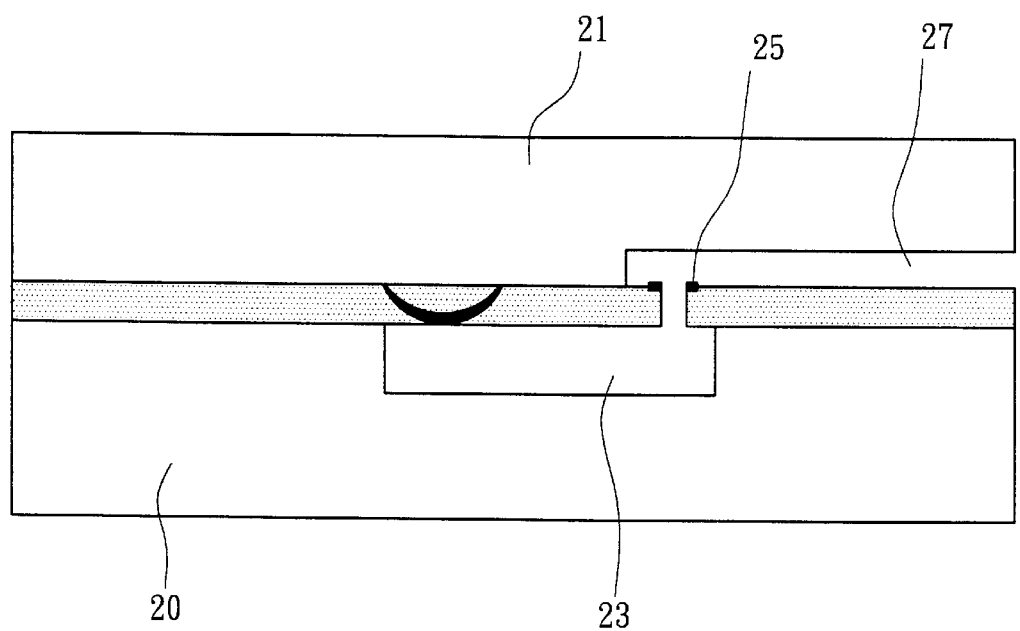
FIG. 3 shows the micro valve actuator of this invention after actuation.

FIG. 1 shows the cross sectional view of a micro valve actuator of this invention prior to actuation. FIG. 2 shows its top view. FIG. 3 shows the micro valve actuator of this invention after actuation.

The micro valve actuator in FIGS. 1–3 contemplates a mechanism for valving microfluidic flow in a normally open configuration using the actuator of this invention. In general, the microfluid valving mechanism in FIG. 1 comprises a primary microfluid channel 22, with a discontinuous section 28, an air vent channel 27 and a vacuum chamber 23.

As shown in FIG. 1, the microfluid valving mechanism comprises a bottom substrate 20 and an upper substrate 21, a microfluid channel 22 inside said upper substrate 21 (FIG. 2), a vacuum chamber 23 under said microfluid channel 22, a diaphragm 24 sealing said vacuum chamber 23, a thin film resistor 25 positioned on said diaphragm 24 and an air vent channel 27 extended to adjacent to said vacuum chamber 23, separated by said diaphragm 24 and said thin film resistor 25.

As shown in FIGS. 1 and 2, the top substrate 21 contains the primary flow channel 22 and the air vent channel 27. The vacuum chamber 23 is prepared in the bottom substrate 20 and extends from a position underneath the air vent channel 27 to a position underneath the primary flow channel 22. The primary flow channel 22 has a discontinuous section 28. This discontinuous section 28 is prepared by providing a block 26 inside the primary flow channel 22 and connected to the upper substrate 21, such that the flow inside the channel 22 may be stopped by the block 26. At the discontinuous section 28 of the primary flow channel 22 the width of the vacuum chamber 23 is enlarged. Due to this enlargement of the vacuum chamber 23, the valve diaphragm 24 above the enlarged area is more flexible and buckles under the pressure differential. This creates a gap 29 under the discontinuous section 28 of the primary flow channel 22 and allows a fluid in the primary channel 22 to flow through the discontinuous section 28. The fluid is able to flow in the direction of the arrow shown in FIG. 2.

As described above, the thin film resistor 25 is positioned between the vacuum chamber 23 and the air vent channel 27. Upon actuation of the actuator by applying a current to resistor 25, heat is generated by the thin film resistor 25 to melt the diaphragm 24. When the diaphragm 24 breaks (See FIG. 3), the vacuum inside the vacuum chamber 23 is released via the air vent channel 27 such that the diaphragm 24 flattens and blocks flow inside the primary flow channel 22 across the gap 28.

As described above, the micro valve actuator of this invention comprises in general a microchannel with a micro valve and a vacuum chamber sealed with a thin diaphragm, on which a thin film resistor is provided. The preparation of the micro valve actuator of this invention will be described in the followings.

The microfluidic actuator of this invention may be divided into two parts, wherein the upper substrate 21 containing a microchannel 22 and the bottom substrate 20 containing the vacuum chamber 23. In the upper substrate 21 provided are a microchannel 22 and an air vent 27 as duct for the released vacuum and in the bottom substrate 20 provided are a thin diaphragm 24 sealing the vacuum chamber 23 and a thin film resistor 25 above the thin diaphragm 24 and the vacuum chamber 23. In the microchannel 22, a section is discontinued by a block 26 to form a micro valve.

The upper substrate 21 and the bottom substrates 20 may be prepared with glass, silicon or plastic with microfabricated channels and chambers respectively. The thin diaphragm 24 may be a metallized polymeric diaphragm, preferably a pressure sensitive cellophane tape, or a pressure sensitive cellophane tape. The thin film resister 25 may be a microfabricated silver film resistor to provide a resistance of approximately 2 ohms, such that it may function as a heater to melt the thin diaphragm 24. The two substrates 20 and 21 and their intermediate layer are vacuum bonded together resulting in a sealed vacuum chamber 23 in the bottom substrate 20. A hot wax melt may be used in bonding the two substrates 20 and 21. For purposes of simplicity, the vacuum chamber 23 is placed in the bottom substrate 20 but it should not be a limitation of this invention. Vacuum processing is then applied to the assembly. The micro valve actuator of this invention is thus prepared.

Prior to actuation, liquid is added into the microchannel 22. While the vacuum chamber 23 has an enlarged area under the discontinuous section 28 of the microchannel, the diaphragm 24 buckles and create a gap 29 under the block 26 inside the microchannel 22, allowing the liquid to flow in the microchannel along the arrow direction in FIG. 2. Upon application of, for example, 3 volts to the thin film resistor 25, the thin diaphragm 24 is melt and broken and the vacuum in the vacuum chamber 23 is released, thereby the diaphragm 24 is deformed to its normal shape and blocks the liquid flow inside the microchannel 22.

The invented micro valve actuator is suited for a microfluidic platform in generating driving forces for valving of liquid samples.

EFFECTS OF THE INVENTION

The present invention discloses an actuation mechanism for micro valves based on the one-time release of vacuum from a small vacuum chamber. Actuation is achieved by applying an electrical current to a thin film resistor which heats and breaks a diaphragm, thereby releasing the vacuum. Since the valves can be integrated into a planar process, highly complex systems can be realized as compared with many microfabricated valves that are not readily integrated in a planar process.

The microfluidic actuator of this invention may be prepared in a chip containing a microfluidic network system. By placing the actuator on the chip itself, the motion of liquids within the microfluidic network system can be controlled by electrical signals alone. This flexibility reduces the complexity of the device operating instruments, since all valves are contained within the device itself. Therefore more portable assays can be realized such as hand held instruments.

As the present invention has been shown and described with reference to preferred embodiments thereof, those skilled in the art will recognize that the above and other changes may be made therein without departing form the spirit and scope of the invention.

What is claimed is:

1. A micro valve actuator to provide a driving force to a micro valve in a microfluidic channel, comprising a vacuum chamber adjacent to said micro valve in said microfluidic channel, a diaphragm to separate said vacuum chamber and said microfluidic channel and a releasing member to break the diaphragm to release a vacuum in said vacuum chamber.

2. The micro valve actuator according to claim 1 wherein said diaphragm comprises a metallized polymeric diaphragm.

3. The micro valve actuator according to claim 1 wherein said diaphragm comprises a pressure sensitive cellophane tape.

4. The micro valve actuator according to claim 1 wherein said vacuum chamber is prepared in a glass, silicon or plastic substrate.

5. The micro valve actuator according to claim 1 wherein said releasing member comprises a heater to generate sufficient heat to break at least a portion of said diaphragm between said vacuum chamber and said microfluidic channel.

6. The micro valve actuator according to claim 5 wherein said heater comprises a thin film resistor positioned adjacent to said diaphragm.

7. A micro valve actuator comprising an air vent channel, a vacuum chamber adjacent to said air vent channel, a diaphragm to separate said vacuum chamber and said air vent channel and a releasing member on said diaphragm to release vacuum in said vacuum chamber.

8. The micro valve actuator according to claim 7 wherein said diaphragm comprises a metallized polymeric diaphragm.

9. The micro valve actuator according to claim 7 wherein said diaphragm comprises a pressure sensitive cellophane tape.

10. The micro valve actuator according to claim 7 wherein said vacuum chamber is prepared in a glass, silicon or plastic substrate.

11. The micro valve actuator according to claim 7 wherein said releasing member comprises a heater to generate sufficient heat to break at least a portion of said diaphragm between said vacuum chamber and said air vent channel.

12. The micro valve actuator according to claim 11 wherein said heater comprises a thin film resistor positioned adjacent to said diaphragm.

13. A micro valve module comprising a substrate, a microfluidic channel with a micro valve prepared in said substrate, a vacuum chamber in said substrate and adjacent to said micro valve in said microfluidic channel, a diaphragm to separate said vacuum chamber and said microfluidic channel and a releasing member to release vacuum in said vacuum chamber.

14. The micro valve module according to claim 13 wherein said diaphragm comprises a metallized polymeric diaphragm.

15. The micro valve module according to claim 13 wherein said diaphragm comprises a pressure sensitive cellophane tape.

16. The micro valve module according to claim 13 wherein said releasing member comprises a heater to generate sufficient heat to break at least a portion of said diaphragm between said vacuum chamber and said microfluidic channel.

17. The micro valve module according to claim 16 wherein said heater comprises a thin film resistor positioned against said diaphragm.

18. The micro valve module according to claim 13 wherein material of said substrate is selected from the group consisted of glass, silicon and plastics.

19. A micro valve module comprising a substrate, a microfluidic channel with a micro valve prepared in said substrate, an air rent channel in said substrate; a vacuum chamber adjacent to said air vent channel, a diaphragm to separate said vacuum chamber and said air vent channel, an air vent channel extended to adjacent to said vacuum chamber and a releasing member on said diaphragm to release vacuum in said vacuum chamber; whereby releasing vacuum in said vacuum chamber brings change to shape of at least a portion of said microfluidic channel adjacent to said micro valve.

20. The micro valve module according to claim 19 wherein said diaphragm comprises a metallized polymeric diaphragm.

21. The micro valve module according to claim 19 wherein said diaphragm comprises a pressure sensitive cellophane tape.

22. The micro valve module according to claim 19 wherein material of said substrate is selected from the group consisted of glass, silicon and plastics.

23. The micro valve module according to claim 19 wherein said releasing member comprises a heater to generate sufficient heat to break at least a portion of said diaphragm between said vacuum chamber and said air vent channel.

24. The micro valve module according to claim 23 wherein said heater comprises a thin film resistor positioned adjacent to said diaphragm.

25. A method to prepare a micro valve module, comprising:

preparing a first substrate containing a microfluidic channel with a micro valve;

preparing a second substrate containing a vacuum chamber sealed with a diaphragm;

positioning a heater on said diaphragm;

bonding said first substrate to said second substrate whereby said vacuum chamber is adjacent to said micro valve in said microfluidic channel, whereby said vacuum chamber and said microfluidic channel are separated by said diaphragm and whereby said heater is positioned at a portion of said diaphragm separating said vacuum chamber and said microfluidic channel.

26. The method according to claim 25 wherein said diaphragm comprises a metallized polymeric diaphragm.

27. The method according to claim 25 wherein said diaphragm comprises a pressure sensitive cellophane tape.

28. The method according to claim 25 wherein said heater comprises a thin film resistor.

29. The method according to claim 28 wherein said heater comprises a microfabricated silver film.

30. The method according to claim 25 wherein material of said substrate is selected from the group consisted of glass, silicon and plastics.

31. A method to prepare a micro valve module, comprising:
- preparing a first substrate containing an air vent and a microfluidic channel with a micro valve;
- preparing a second substrate containing a vacuum chamber sealed with a diaphragm;
- positioning a heater on said diaphragm;
- bonding said first substrate to said second substrate whereby said vacuum chamber is adjacent to said micro valve and said air vent channel, whereby said vacuum chamber and said air vent channel are separated by said diaphragm, whereby said heater is positioned at a portion of said diaphragm separating said vacuum chamber and said air vent channel and whereby releasing vacuum in said vacuum chamber brings change to shape of at least a portion of said microfluid channel adjacent to said micro valve.

32. The method according to claim 31 wherein said diaphragm comprises a metallized polymeric diaphragm.

33. The method according to claim 31 wherein said diaphragm comprises a pressure sensitive cellophane tape.

34. The method according to claim 31 wherein material of said substrate is selected from the group consisted of glass, silicon and plastics.

35. The method according to claim 31 wherein said heater comprises a thin film resistor positioned adjacent to said diaphragm.

36. The method according to claim 35 wherein said heater comprises a microfabricated silver film.

* * * * *